United States Patent [19]

Terrell

[11] Patent Number: 4,682,507

[45] Date of Patent: Jul. 28, 1987

[54] MATERIAL SAMPLING APPARATUS

[75] Inventor: Michael S. Terrell, Charlotte, N.C.

[73] Assignee: Duke Power Company, Charlotte, N.C.

[21] Appl. No.: 631,086

[22] Filed: Jul. 16, 1984

[51] Int. Cl.[4] .......................... G01N 1/12; G01N 1/20
[52] U.S. Cl. ............................ 73/863.57; 73/863.83;
73/863.86; 73/863.52; 73/863.73; 73/863.56
[58] Field of Search .......... 73/863.56, 863.86, 863.81,
73/863.57, 864.73, 863.51, 863.52, 863.71,
863.72, 863.73, 863.83, 863.84

[56] References Cited

U.S. PATENT DOCUMENTS

| | | | |
|---|---|---|---|
| 3,064,481 | 11/1962 | Alexander | 73/863.83 |
| 3,084,555 | 4/1963 | Van Dop | 73/863.83 |
| 3,087,334 | 4/1963 | Brown | 73/863.83 X |
| 3,109,306 | 11/1963 | Funk | 73/863.83 |
| 3,348,419 | 10/1967 | Addison | 73/863.83 |
| 3,555,910 | 1/1971 | Spence et al. | 73/863.83 |
| 3,751,992 | 8/1973 | Morgan | 73/863.83 |
| 3,782,200 | 1/1974 | Maas | 73/863.51 |
| 4,085,618 | 4/1978 | Collins, Jr. | 73/863.73 |
| 4,346,609 | 8/1982 | Diesel | 73/863.51 X |
| 4,462,265 | 7/1984 | Rein | 73/863.72 X |

FOREIGN PATENT DOCUMENTS

| | | | |
|---|---|---|---|
| 815802 | 6/1969 | Canada | 73/863.57 |
| 2250111 | 5/1975 | France | 73/863.83 |
| 583383 | 12/1977 | U.S.S.R. | 73/863.83 |
| 634148 | 11/1978 | U.S.S.R. | 73/863.51 |

Primary Examiner—Jerry W. Myracle
Assistant Examiner—Tom Noland
Attorney, Agent, or Firm—Shefte, Pinckney & Sawyer

[57] ABSTRACT

Apparatus for removing a sample from a material conveying conduit and delivering the sample to a remote testing or other deposit location without any manual handling of the sample, including a valve having a tubular housing fixed to the conduit to extend interiorly therethrough transversely of the material flow path and interiorly defining a collection chamber, a port in the housing facing upstream of the material flow path and opening to the collection chamber, a truncated piston arranged rotatably within the collection chamber with its truncated end at the port to close the port in one rotational position and open the port in another, corresponding passageways formed off-center axially through the piston and through an adjacent interior wall of the tubular housing to be in alignment in the closed condition of the valve and out of alignment in the open condition thereof, a compressed air source connected to the passageways in the interior wall and a conduit extending from the collection chamber outwardly through the tubular housing to the remote testing location. The piston is rotated to its port opening position to collect a material sample, then rotated to its port closing position to align its passageways with those of the interior wall, and the pressurized air source is activated to expel the collected material from the collection chamber and carry it through the conduit to the testing location.

9 Claims, 3 Drawing Figures

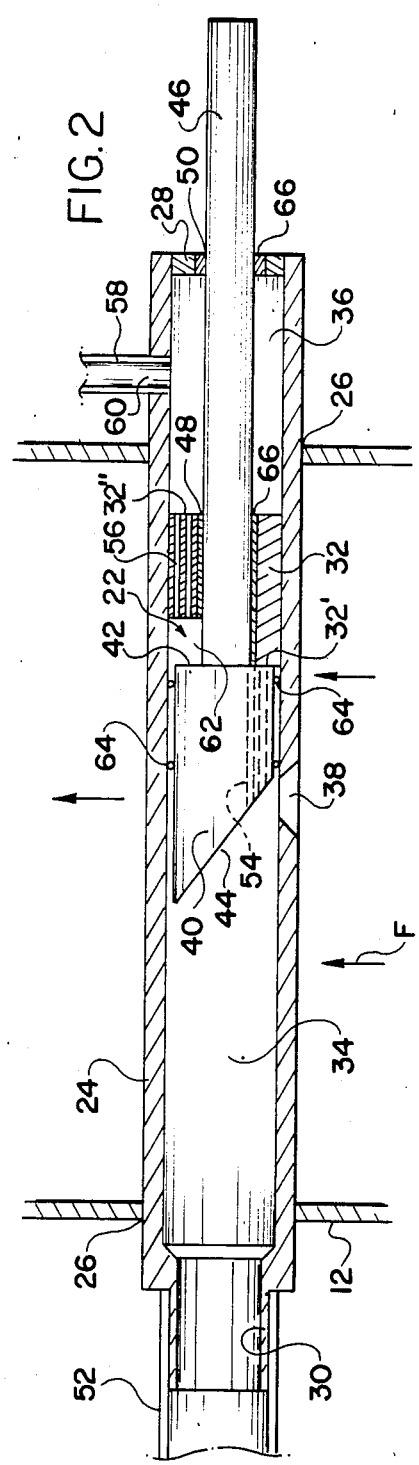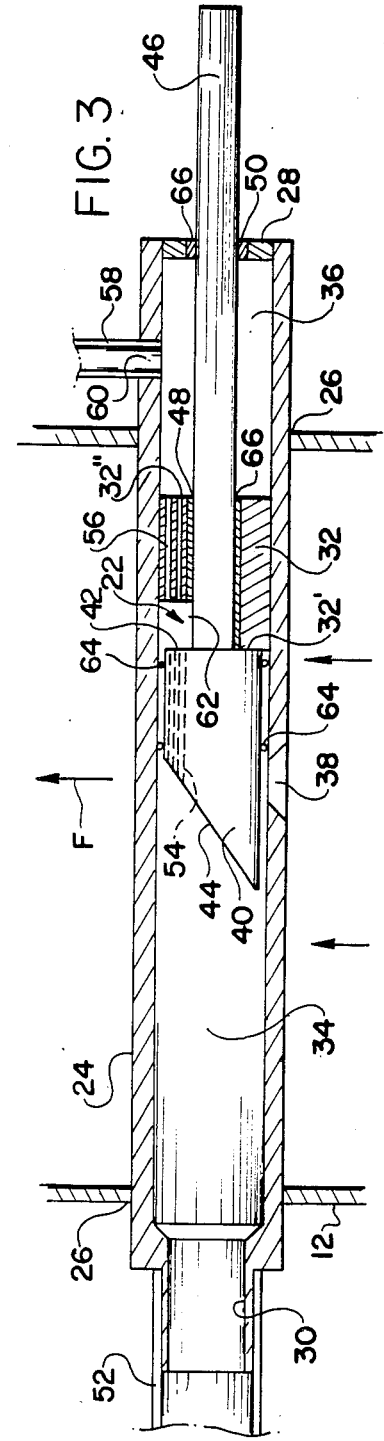

MATERIAL SAMPLING APPARATUS

BACKGROUND OF THE INVENTION

The present invention relates generally to apparatus for obtaining a sample from a material conveying conduit system, particularly those handling toxic or other hazardous or dangerous materials which must be contained and cannot be manually handled.

In various material processing, treating and like operations wherein a material is conveyed through a conduit system, it is often desirable or necessary to monitor periodically the composition or other characteristics of the material. For this purpose, a wide variety of devices and apparatus are known and available for withdrawing a sample of the material from the conduit system. Typically, the collection device or apparatus extends through a wall of the conduit system and is selectively openable and closeable to collect a sample quantity of the conveyed material and to withdraw the sample to a separable container outside the conduit system in which the sample may be transported to a laboratory or other location for testing or analysis or otherwise handled as considered necessary or desirable. Representative examples of such apparatus are disclosed in U.S. Pat. Nos. 2,558,387; 3,109,306; 3,555,910; and 4,147,062.

For the most part, such apparatus and devices are entirely satisfactory for many sampling applications. However, such apparatus and devices are generally considered undesirable for safety reasons in obtaining and handling samples taken from systems conveying toxic or other hazardous or dangerous materials such as radioactive waste slurries, toxic chemicals and gases, and the like. In such applications, the required transferring of the material from the collector to a container and the manual handling and transportation of the container create unacceptably high risks of accidental breakage, loss or other escape or release of the material which may result in contamination or injury of the personnel involved. One known sampling apparatus has been proposed utilizing an enclosed conveying system for transporting a sample from a collecting device to a testing or analysis device without manual handling, such apparatus being disclosed in U.S. Pat. No. 3,362,228. However, such apparatus is not believed to have achieved any significant degree of acceptability and use and, in any event, is not particularly designed and intended for applications handling hazardous materials.

The present invention provides an improved sampling apparatus generally of the latter above-described type which is particularly provided with a simple and reliable construction well adapted and designed for obtaining samples from conveying systems handling hazardous materials and delivering the samples to a remote deposit location without any required manual handling of the samples.

SUMMARY OF THE INVENTION

Briefly described, the present apparatus includes a valve arrangement fixedly disposed in the conduit system from which material samples are to be taken, the valve arrangement being selectively openable and closeable for capturing a portion of the material as the sample. A discharge conduit provides communication between the valve arrangement and the remote deposit location outside the conduit system for conveying the sample thereto. An arrangement is provided for directing a pressurized fluid through the valve arrangement and the discharge conduit to expel the sample from the valve arrangement and carry through the discharge conduit. In this manner, the sample is collected and conveyed to the deposit location without manual handling of the sample to prevent escape thereof.

In the preferred embodiment, the sampling apparatus is preferably incorporated in a conduit system carrying a moving stream of a toxic material. The valve arrangement includes a sample receiving tube disposed to extend sealably through the conduit system transversely through the moving material stream. The sample receiving tube has a cylindrical interior sample collection chamber and a port extending from an intermediate location in the chamber outwardly through the tube to face in an upstream direction relative to the material flow for passage through the port into the collection chamber of the sample portion of the material. An interior wall is provided in the collection chamber on one side of the port and a discharge opening extends from the chamber on the other side of the port outwardly through the tube to the outside of the conduit system. A cylindrical piston is closely fitted rotatably in the collection chamber to one side of the port, the piston having one radial end surface in abutment with the interior wall of the collection chamber and an opposite truncated end surface disposed at the port for rotation between a port closing position wherein the truncated end surface faces away from the port and the adjacent cylindrical periphery of the piston closes the port to prevent material passage therethrough and a port opening position wherein the truncated end surface faces toward the port at a spacing therefrom to open the port to permit material passage therethrough. An appropriate arrangement is provided for rotatably moving the piston between the port opening and closing positions to capture the material sample in the collection chamber. A passageway extends through the interior wall of the collection chamber and another passageway extends through the piston from the truncated end surface to a location on the radial end surface to be in communicative alignment with the interior wall passageway in the port closing position of the piston and to be out of alignment and communication with the interior wall passageway in the port opening position of the piston. The discharge conduit is joined in fluid communication with the discharge opening of the tube. The pressurized fluid arrangement is joined in fluid communication with the passageway through the interior wall of the collection chamber and is adapted to deliver pressurized air therethrough.

BRIEF DESCRIPTION OF THE DRAWINGS

FIG. 2 is a horizontal cross-sectional view of the sampling apparatus of FIG. 1 taken along line 2—2 thereof showing the apparatus in its open condition; and FIG. 3 is another horizontal cross-sectional view of the sampling apparatus also taken along line 2—2 of FIG. 1 showing the apparatus in its closed condition.

DESCRIPTION OF THE PREFERRED EMBODIMENT

Figure 1:
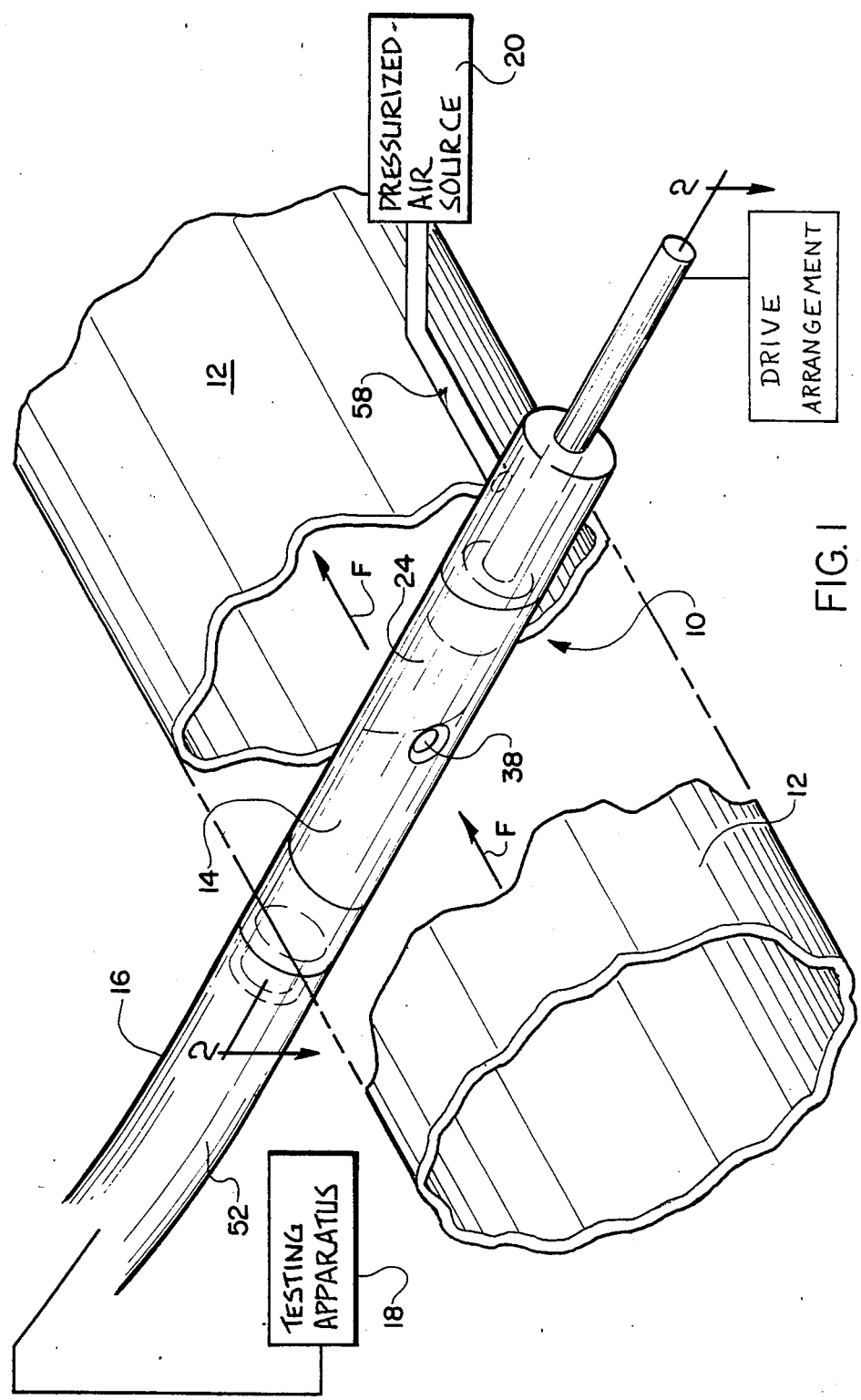
FIG. 1 is a perspective view of the preferred embodiment of the sampling apparatus of the present invention incorporated in a conduit system.

Referring now to the accompanying drawings, and initially to FIG. 1, the sampling apparatus of the present invention is indicated generally at 10 as preferably embodied in a closed conduit system, a conduit section of which is representatively indicated at 12, used in nuclear electrical power station low level radiation processing applications for transporting a moving air stream of entrained radioactive dust, a moving stream of radioactive waste slurry, or like radioactive waste material. Basically, the apparatus 10 includes a collection valve 14 fixedly positioned in the conduit 12 and openable and closeable to capture a sample of the material being conveyed therethrough. A discharge conduit arrangement 16 provides fluid communication between the valve 14 and a remote deposit location for the sample material, indicated generally at 18. A source of pressurized air 20 is connected with the valve 14 for expelling the collected material sample from the valve and conveying it through the conduit arrangement 16. An auxiliary valve arrangement, generally indicated at 22 in FIG. 2, coordinates fluid communication between the valve 14 and the pressurized air source 20 in relation to the open and closed condition of the valve 14 so that the auxiliary valve arrangement 22 is open to permit pressurized air flow into the valve 14 when in its closed condition and to prevent such pressurized air flow when the valve 14 is in its open condition.

As best seen in FIGS. 2 and 3, the valve 14 includes a cylindrical tubular housing 24 which extends diametrically through the conduit 12 perpendicularly to the direction of material flow therthrough, as indicated by the directional arrows F, with the ends of the tube 24 extending outwardly through openings 26 in the opposite side walls of the conduit 12 and being sealably affixed rigidly thereto. One end of the tubular housing 24 is closed by an end wall 28, the other end of the tubular housing 24 opening outwardly through a projecting sleeve portion 30. An interior dividing wall 32 extends diametrically across the tubular housing 24 to define a material collection chamber 34 between one wall face 32' and the open end of the tubular housing 24 and to define an air inlet chamber 36 between the other wall face 32" and the end wall 28 at the closed end of the tubular housing 24. A material receiving port 38 is formed through the tubular housing 24 opening to the collection chamber 34 generally adjacent the dividing wall 32 at the side of the tubular housing 24 facing upstream of the direction of material flow F through the conduit 12 for permitting passage of the material into the collection chamber 34.

A cylindrical valve member in the form of a piston 40 is closely fitted rotatably in the collection chamber 34 to extend from the dividing wall 32 to just beyond the material receiving port 38. One end of the piston 40 has a radial face 42 positioned in abutment with the face 32' of the dividing wall 32. The opposite end of the piston 40 is truncated at a sufficient angle to the axis of the piston 40 to leave an elliptical face 44 extending from one axial side of the port 38 to the other. Thus, the rotational disposition of the piston 40 within the tubular housing 24 controls the opening and closing of the port 38. In a position wherein the truncated end face 44 of the piston 40 faces toward the port 38, as shown in FIG. 2, the port 38 is open to fluid communication with the collection chamber 34 to permit passage of a portion of the material stream flowing through the conduit 12 into the collection chamber 34. However, in a position of the piston 40 wherein its truncated end face 44 faces away from the port 38 with the cylindrical periphery of the piston 40 covering the port 38, as shown in FIG. 3, the port 38 is closed to communication with the collection chamber 34 to prevent passage of material flowing through the conduit 12 into the collection chamber 34.

An operating shaft 46 is connected to and extends axially from the center of the radial end face 42 of the piston 40 through a central bore 48 in the dividing wall 32 and through a corresponding bore 50 in the end wall 28. As will be understood, the operating shaft 46 may be connected by any suitable mechanical arrangement 55 to actuate rotational or reciprocal movement of the piston 40 between its port opening and closing positions of FIGS. 2 and 3.

The deposit location 18 preferably is a suitable apparatus or device for performing desired testing or analysis of material samples obtained from the conduit section 12 by the valve 14 and ordinarily will be located in a laboratory or other appropriate testing facility at a remote location from the conduit section 12. The discharge conduit arrangement 16 is a continuous, enclosed tubular conduit 52 fitted at one end thereof to the sleeve portion 30 at the open end of the tubular housing 24 and extending therefrom to and being suitably connected at the opposite end of the conduit 52 to the testing apparatus or device at the deposit location 18 to provide fluid communication between the collection chamber 34 and the deposit location 18 for conveyance thereto of material collected in the chamber 34.

The auxiliary valve arrangement 22 includes at least one, and preferably several, passageways 54 bored axially through the piston 40 in a selected area spaced radially outwardly from the rotational axis of the piston 40. At least one passageway 56, and preferably a corresponding number of such passageways 56, are bored in a corresponding relative arrangement to one another axially through the dividing wall 32 in an off-center area thereof to be aligned with the passageways 54 in the port closing position of the piston 40, as seen in FIG. 3, but to be out of alignment with the passageways 54 in the port opening position of the piston 40, as seen in FIG. 2. In this manner, the passageways 54,56 of the auxiliary valve arrangement 22 coordinate fluid communication between the collection chamber 34 and the air inlet chamber 36 in relation to the open or closed condition of the valve 14 to permit such fluid communication in the closed condition of the valve 14 but not in the open condition thereof.

A tubular conduit 58 extends from the pressurized air source 20 through a port 60 opening through the tubular housing 24 to the air inlet chamber 36 to provide fluid communication between the pressurized air source 20 and the air inlet chamber 36. It will thus be understood that in the port closing position of the piston 40, an open fluid flow path exists from the pressurized air source 20 through the conduit 58, the air inlet chamber 36, the passageways 54,56, the collection chamber 34, and the tubular conduit 52, to the testing apparatus or device at the deposit location 18. To enhance the passage of the pressurized air stream through the passageways 54,56, a portion of the face 32' of the dividing wall 32 in the area where the passageways 56 are formed is cut away to provide an air expansion area 62 for the air stream intermediate the passageways 54,56 so that the above-described flow path is completed with the piston 40 is in its port closing position even without exact alignment of the passageways 54 with the passageway 56.

Appropriate conventional seals 64 are provided around the cylindrical periphery of the piston 40 to provide sealing engagement with the interior cylindrical surface of the collection chamber 34. Other seals 66 are provided around the operating shaft 46 at the dividing wall 32 and the end wall 28 to seal the air inlet chamber 36.

The components of the sampling apparatus 10 are constructed of suitable material selected to resist corrosion, abrasion and other deterioration from exposure to the radioactive materials with which the apparatus 10 is used. For example, the tubular housing 24 and the piston 40 may be constructed of stainless steel, whereby the valve 14 is suitable not only for use in radioactive material conveying systems but also in chemical and substantially any other hazardous material conveying system. Similarly, the seals 64,66 are constructed of selected materials to provide the necessary sealing capabilities together with appropriate radiation, chemical and temperature resistance. A number of suitable synthetic rubbers are known which adequately meet these criteria, e.g. VITON brand synthetic rubber manufactured by E. I. duPont de Nemours & Co., of Wilmington, Del., as well as generic synthetic rubbers such as EPDM and Buna-N.

In the operation of the sampling apparatus 10, the piston 40 is normally retained in its port closing position of FIG. 3 to prevent passage of the material flowing through the conduit section 12 from passing into the collection chamber 34. When it is desired to obtain a sample of the material in the conduit section 12, the piston 40 is rotated, either manually or mechanically, to its port opening position of FIG. 2 to uncover the port 38 and permit passage of a portion of the material flowing through the conduit section 12 into the collection chamber 34. The piston 40 is maintained in its port opening position for a predetermined time to allow a suitable sample quantity of the material to enter the collection chamber 34, after which the piston 40 is rotated to return it to its port closing position. Thereupon, the pressurized air source 20 is operated to convey pressurized air through the then completed fluid flow path above-described to expel the collected sample of the material from the collection chamber 34 outwardly through the sleeve 30 at the open end of the tubular housing 24 and to carry the expelled material through the tubular conduit 52 and deposit the material at the testing apparatus at the deposit location 18.

As will be understood, it may be desirable to use the apparatus 10 to collect plural samples of the material at periodic timed intervals to facilitate a continuous monitoring of the consistency of the material flowing through the conduit section 12. In such cases, an appropriate timed mechanical arrangement is provided in operative asociation with the operating shaft 46 to provide appropriate reciprocal rotational or continuous rotational movement of the piston 40 between its port opening and port closing positions at the desired timed interval and to maintain the piston 40 in its port opening position each such time for a desired predetermind length of time. Depending upon the frequency at which sample quantities are to be periodically obtained, the pressurized air source 20 may be run continuously or may be operatively associated with the operating mechanism for the shaft 46 to be actuated upon each rotation or reciprocal manipulation thereof. In other applications, the apparatus 10 may be used sporadically to collect material samples. In such cases, of course, an operating mechanism associated with the shaft 46 may also be utilized or, alternatively, the shaft 46 may be manually actuated for sampling operation. In such latter cases, an operating handle (not shown) may be provided on the outwardly extending end of the shaft 46 for facilitating the manual operation thereof. Ordinarily, in such cases, the pressurized air source 20 is manually actuated as well, but could be set up as desired to run continuously.

Advantageously, the sampling apparatus 10 will thus be understood to be effective to collect a material sample and convey it to the testing or analysis device at the remote deposit location 18 without any required manual handling of the sample material at any time. Therefore, the normal risks of accidental breakage, loss or other escape of the collected sample material which exists with conventional sampling apparatus of the type that simply collect the sample in a container which must be manually transported to the testing location, are virtually entirely eliminated. Furthermore, the apparatus 10 of the present invention is of an extremely simple construction, the only moving component of which is the assembly of the piston 40 and shaft 46. Therefore, the apparatus 10 is highly reliable and sturdy in operation as well as being inexpensive to manufacture and easy to operate.

Those persons skilled in the art will understand that, while the present invention has been described in the preferred embodiment thereof as the apparatus 10 for use in sampling radioactive materials, the present invention is susceptible of a much broader utility. For example, the apparatus of the present invention is equally well adapted for use in obtaining samples from conveying systems for substantially any other toxic or hazardous material of either solid, liquid or gaseous composition, as well as in many other material conveying systems, without departing from the scope or substance of the present invention. Accordingly, it is to be understood that the present invention is not limited to the particular preferred embodiment herein described which has been set forth solely as exemplary of the present invention for purposes of illustration thereof. All adaptations, modifications, variations and equivalent arrangements which would be apparent from or suggested to those persons skilled in the art by the foregoing disclosure are within the scope and substance of the present invention, which is to be limited only by the claims appended hereto and the equivalents thereof.

I claim:

1. An apparatus for removing a sample from a moving stream of a material flowing in a predetermined direction through a conduit and delivering said sample to a deposit location outside said conduit, said apparatus comprising:
   a. valve means disposed in said conduit for collecting said material sample, said valve means including a fixed valve housing defining an interior sample collection chamber, a port in said housing facing in an upstream direction relative to said direction of material conveyance for passage therethrough into said collection chamber of a portion of said material as said sample, and a valve member selectively movable relative to said collection chamber between positions opening and closing said port for permitting and preventing passage of said material through said port;
   b. discharge conduit means communicating with said collection chamber and extending therefrom to said deposit location for conveying said sample thereto; and c. means for directing a pressurized fluid through said material collection chamber and into said conduit means for expelling said material sample from said collection chamber and carrying said sample through said conduit means, whereby said sample is collected and conveyed to said deposit location without manual handling of said sample to aid in preventing escape thereof.

2. An apparatus for removing and delivering a material sample according to claim 1 and characterized further by auxiliary valve means for preventing fluid communication between said fluid directing means and said collection chamber when said valve member is in its port opening position to prevent the direction of said pressurized fluid through said collection chamber when said sample is being collected and for permitting fluid communication between said fluid directing means and said collection chamber when said valve member is in its port closing position to actuate direction of said pressurized fluid through said valve means after said sample has been collected.

3. An apparatus for removing and delivering a material sample according to claim 2 and characterized further in that said auxiliary valve means includes a first fluid passageway extending through said valve housing from a location of fluid communication with said fluid directing means to an opening into said collection chamber at said valve member and a second fluid passageway extending through said valve member to be in communicative alignment with said first fluid passageway in the port closing position of said valve member and to be out of communicative alignment with said first fluid passageway in the port opening position of said valve member.

4. An apparatus for removing and delivering a material sample according to claim 3 and characterized further in that said valve member is rotatably disposed in said collection chamber in axial end abutment with an interior wall thereof for rotational movement between the port opening and closing positions, said second fluid passageway being formed axially through said valve member at a spacing from the axis of its rotational movement and said first passageway being formed in said interior wall of said collection chamber.

5. An apparatus for removing and delivering a material sample according to claim 4 and characterized further in that said collection chamber is cylindrical and said valve member is a cylindrical piston having a truncated end surface at said port for facing away from said port in the port closing position of said piston with the cylindrical periphery of said piston covering said port and for facing toward said port at a spacing therefrom in the port opening position of said piston to open said port to said collection chamber.

6. The apparatus of claim 5 in combination with a material conveying system including said conduit.

7. The apparatus of claim 1 in combination with a material conveying system including said conduit.

8. Apparatus for removing a material sample from a moving stream of a toxic material flowing in a predetermined direction through a closed conduit system and delivering said sample to a remote deposit location outside said conduit system, said apparatus comprising:

a. a sample receiving tube of fixed disposition extending sealably through said conduit system transversely through said moving stream, said sample receiving tube having a cylindrical interior sample collection chamber, a port extending from an intermediate location in said chamber outwardly through said tube for orientation within said conduit system to face in an upstream direction relative to said direction of material flow for passage through said port into said collection chamber of a portion of said material as said sample, an interior wall on one side of said port, and a discharge opening extending from said chamber on the other side of said port outwardly through said tube to the outside of said conduit system;

b. a cylindrical piston closely fitted rotatably in said collection chamber to said one side of said port, said piston having a radial surface forming one end of said piston in abutment with said interior wall of said collection chamber and a truncated surface forming the opposite end of said piston disposed at said port for rotation between a port closing position wherein the truncated end surface faces away from said port and the cylindrical periphery of said piston at said truncated end closes said port to prevent passage of said material therethrough and a port opening position wherein the truncated end surface faces toward said port at a spacing therefrom to open said port to permit passage of said material therethrough;

c. means for rotatably moving said piston between said port opening and closing positions to capture said sample in said collection chamber;

d. a passageway through said interior wall of said collection chamber and a passageway extending through said piston from said truncated end surface to a location on said radial end surface to be in communicative alignment with said interior wall passageway in said port closing position of said piston and to be out of alignment and communication with said interior wall passageway in said port opening position of said piston;

e. discharge conduit means communicating with said discharge opening of said tube and extending therefrom to said deposit location for conveying said sample thereto; and f. means providing communication between a source of pressurized air and said interior wall passageway for directing said pressurized air therethrough and through said piston passageway, said collection chamber and said discharge conduit means in said port closing position of said piston for expelling said sample from said collection chamber and carrying said sample through said conduit means to said deposit location;

whereby said sample is collected and conveyed to said deposit location without any manual handling of said sample to aid in preventing escape thereof.

9. The apparatus of claim 8 in combination with said closed conduit system.

* * * * *

UNITED STATES PATENT OFFICE
CERTIFICATE OF CORRECTION

Patent No. 4,682,507    Dated July 28, 1987

Inventor(s) Michael S. Terrell

It is certified that error appears in the above-identified patent and that said Letters Patent are hereby corrected as shown below:

Col. 3, Line 29, delete "therthrough" and insert therefor — therethrough — .

Col. 5, Line 50, delete "consistency" and insert therefor — constituency — .

Signed and Sealed this
Thirtieth Day of August, 1988

*Attest:*

DONALD J. QUIGG

*Attesting Officer*    *Commissioner of Patents and Trademarks*